(12) United States Patent
Ranucci et al.

(10) Patent No.: US 10,368,870 B2
(45) Date of Patent: Aug. 6, 2019

(54) SURGICAL FASTENER

(71) Applicant: C.R. Bard, Inc., Murray Hill, NJ (US)

(72) Inventors: Kevin J. Ranucci, Warwick, RI (US);
Saurav V. Gupta, Medway, MA (US);
Keith A. Grider, Chicago, IL (US);
Derek Leatzow, Chicago, IL (US)

(73) Assignee: C.R. Bard, Inc., Murray Hill, NJ (US)

(*) Notice: Subject to any disclaimer, the term of this patent is extended or adjusted under 35 U.S.C. 154(b) by 114 days.

(21) Appl. No.: 14/075,354

(22) Filed: Nov. 8, 2013

(65) Prior Publication Data

US 2015/0133970 A1 May 14, 2015

(51) Int. Cl.
*A61B 17/08* (2006.01)
*A61B 17/064* (2006.01)
*A61B 17/068* (2006.01)

(52) U.S. Cl.
CPC .......... *A61B 17/08* (2013.01); *A61B 17/064* (2013.01); *A61B 17/068* (2013.01); *A61B 2017/0649* (2013.01)

(58) Field of Classification Search
CPC .......... A61B 17/068; A61B 2017/0649; A61B 17/10; A61B 17/064; A61B 2017/0647; A61B 2017/0648; F16B 1/0014; F16B 37/12; F16B 5/07; F16B 21/125
USPC ............... 606/139, 151; 411/392, 411, 438; 52/506, 512
See application file for complete search history.

(56) References Cited

U.S. PATENT DOCUMENTS

| | | |
|---|---|---|
| 2,407,879 A | 9/1946 | Haas |
| 3,229,374 A | 1/1966 | Comorau |
| 4,318,651 A | 3/1982 | Ragen |
| 4,762,453 A | 8/1988 | DeCaro |

(Continued)

FOREIGN PATENT DOCUMENTS

| | | |
|---|---|---|
| EP | 0 663 184 A1 | 7/1995 |
| GB | 2417208 | 2/2006 |

(Continued)

OTHER PUBLICATIONS

U.S. Appl. No. 14/075,398, filed Nov. 8, 2013, Ranucci et al.

(Continued)

*Primary Examiner* — George J Ulsh
(74) *Attorney, Agent, or Firm* — Wolf, Greenfield & Sacks, P.C.

(57) ABSTRACT

A surgical fastener is provided for various surgical fastening applications, including attaching an implantable prosthesis, such as a soft tissue repair fabric, to tissue and/or muscle. The surgical fastener may include a coil body and a head attached to the coil body. The head may include at least one external thread adapted to engage with a corresponding internal thread of a delivery device. The head may include a through hole adapted to receive a rod therethrough for guiding and/or driving the surgical fastener from the delivery device. The through hole may have a non-circular configuration that complements at least a portion of the shape of a non-circular rod. The coil body may also define a channel with a non-circular configuration. The non-circular through hole and/or channel may be engaged and rotated by the non-circular rod to rotate the surgical fastener for delivery and insertion of the fastener into the prosthesis and/or tissue.

32 Claims, 3 Drawing Sheets

(56) References Cited

U.S. PATENT DOCUMENTS

| | | | |
|---|---|---|---|
| 4,917,554 A | 4/1990 | Bronn | |
| 5,256,133 A | 10/1993 | Spitz | |
| 5,733,307 A * | 3/1998 | Dinsdale | A61B 17/0401 606/104 |
| 5,904,696 A | 5/1999 | Rosenman | |
| 6,383,187 B2 | 5/2002 | Tormala et al. | |
| 6,409,445 B1 | 6/2002 | Beale et al. | |
| 7,189,251 B2 | 3/2007 | Kay | |
| 7,862,573 B2 | 1/2011 | Darois et al. | |
| 7,867,252 B2 | 1/2011 | Criscuolo et al. | |
| 8,087,142 B2 | 1/2012 | Levin et al. | |
| 8,231,639 B2 | 7/2012 | Bolduc et al. | |
| 8,292,933 B2 | 10/2012 | Zergiebel | |
| 8,343,176 B2 | 1/2013 | Criscuolo et al. | |
| 8,382,778 B2 | 2/2013 | Criscuolo et al. | |
| 9,072,511 B2 | 7/2015 | Tegzes | |
| 9,445,814 B2 | 9/2016 | Ranucci et al. | |
| 9,615,830 B2 | 4/2017 | Ranucci et al. | |
| 9,675,353 B2 | 6/2017 | Ranucci et al. | |
| 2002/0055738 A1* | 5/2002 | Lieberman | A61B 17/70 606/246 |
| 2003/0181913 A1 | 9/2003 | Lieberman et al. | |
| 2004/0193217 A1 | 9/2004 | Lubbers et al. | |
| 2005/0187568 A1 | 8/2005 | Klenk et al. | |
| 2007/0038220 A1 | 2/2007 | Shipp | |
| 2007/0088390 A1* | 4/2007 | Paz | A61B 17/0401 606/232 |
| 2007/0140810 A1 | 6/2007 | Itou et al. | |
| 2007/0250064 A1 | 10/2007 | Darois et al. | |
| 2008/0004626 A1 | 1/2008 | Glazer et al. | |
| 2009/0118776 A1* | 5/2009 | Kelsch | A61B 17/0401 606/325 |
| 2010/0010520 A1 | 1/2010 | Takahashi et al. | |
| 2010/0145393 A1 | 6/2010 | Fallin et al. | |
| 2010/0256690 A1 | 10/2010 | Appenzeller et al. | |
| 2010/0274266 A1 | 10/2010 | Rimer et al. | |
| 2011/0022065 A1 | 1/2011 | Shipp | |
| 2011/0087240 A1 | 4/2011 | Shipp | |
| 2011/0092992 A1 | 4/2011 | Darois et al. | |
| 2011/0295282 A1 | 12/2011 | Glick et al. | |
| 2011/0295319 A1 | 12/2011 | Duplessis et al. | |
| 2012/0022557 A1 | 1/2012 | Cabiri et al. | |
| 2012/0101526 A1 | 4/2012 | Bennett | |
| 2013/0131700 A1 | 5/2013 | Criscuolo et al. | |
| 2013/0338706 A1* | 12/2013 | Jimenez | A61B 17/0057 606/213 |
| 2014/0243855 A1 | 8/2014 | Sholev et al. | |
| 2015/0133964 A1 | 5/2015 | Ranucci et al. | |
| 2015/0133971 A1 | 5/2015 | Ranucci et al. | |
| 2015/0133972 A1 | 5/2015 | Ranucci et al. | |
| 2015/0152908 A1 | 6/2015 | Schwarzbich | |
| 2017/0027560 A1 | 2/2017 | Ranucci et al. | |
| 2017/0143340 A1 | 5/2017 | Ranucci et al. | |
| 2017/0231632 A1 | 5/2017 | Ranucci et al. | |

FOREIGN PATENT DOCUMENTS

| | | |
|---|---|---|
| WO | WO 1997/07744 A1 | 3/1997 |
| WO | WO 2002/09625 A1 | 2/2002 |
| WO | WO 2005/004727 A1 | 1/2005 |
| WO | WO 2005/081936 A2 | 9/2005 |
| WO | WO 2011/092692 A2 | 8/2011 |
| WO | WO 2012/176195 A2 | 12/2012 |
| WO | WO 2013/046115 A1 | 4/2013 |

OTHER PUBLICATIONS

U.S. Appl. No. 14/075,441, filed Nov. 8, 2013, Ranucci et al.
U.S. Appl. No. 14/075,464, filed Nov. 8, 2013, Ranucci et al.
[No Author Listed], Winding. (n.d.). Dictionary.com Unabridged. Retrieved Apr. 14, 2016 from Dictionary.com website. 12 Pages. Http://www.dictionary.com/browse/winding.

* cited by examiner

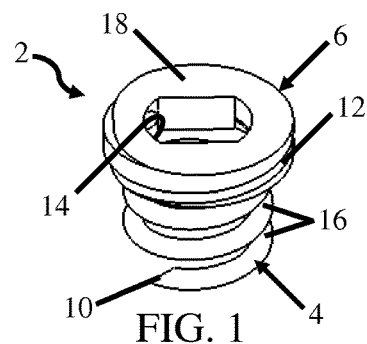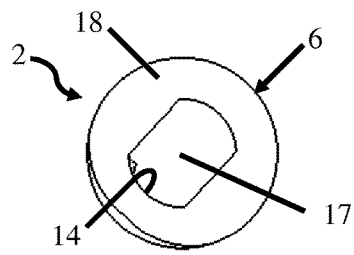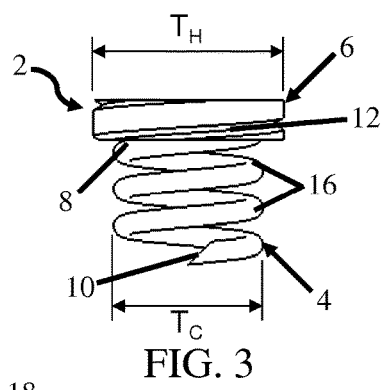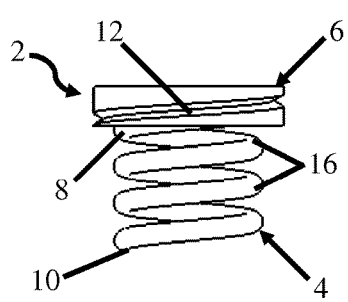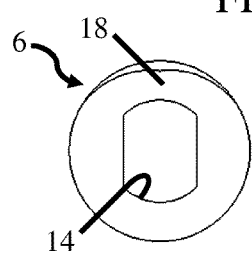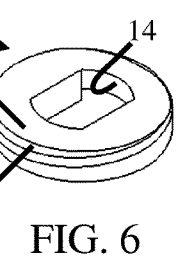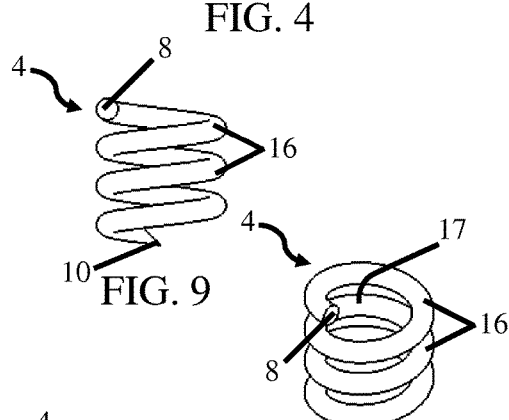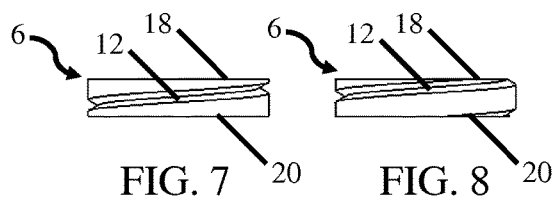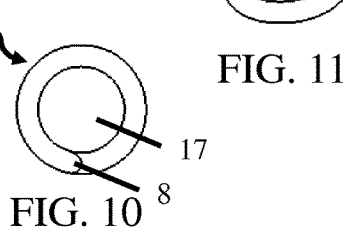

SURGICAL FASTENER

FIELD

Disclosed embodiments are related to a surgical fastener, and more particularly, to a surgical fastener that includes a coil body with an attached head.

BACKGROUND

Surgical fasteners are widely used in many different medical procedures. For example, staples, sutures, clips and other fasteners are commonly used in laparoscopic and open surgical procedures.

SUMMARY

In one aspect of the invention, a surgical fastener comprises a coil body and a separate head attached to the coil body. The coil body includes a plurality of coil windings and has a proximal end and a distal end. The proximal end of the coil body is attached to the head. The head includes at least one external thread adapted to engage with a corresponding internal thread of a delivery device. The head further includes a non-circular through hole adapted to receive a rod therethrough to guide and/or drive the surgical fastener from the delivery device.

In another aspect of the invention, a surgical fastener comprises a coil body and a separate head attached to the coil body. The coil body includes a plurality of coil windings and has a proximal end and a distal end. The proximal end is attached to the head. The coil body defines a non-circular channel adapted to receive a rod of a delivery device therethrough. The head includes a through hole adapted to receive the rod therethrough to guide and/or drive the surgical fastener from the delivery device.

BRIEF DESCRIPTION OF DRAWINGS

Various embodiments of the invention will now be described, by way of example, with reference to the accompanying drawings, in which:

FIG. 1 is a schematic perspective view of a surgical fastener;

FIG. 2 is a schematic top view of the surgical fastener of FIG. 1;

FIG. 3 is a schematic front view of the surgical fastener of FIG. 1;

FIG. 4 is a schematic side view of the surgical fastener of FIG. 1;

FIG. 5 is a schematic top view of a surgical fastener head;

FIG. 6 is a schematic perspective view of the surgical fastener head of FIG. 5;

FIG. 7 is a schematic front view of the surgical fastener head of FIG. 5;

FIG. 8 is a schematic side view of the surgical fastener head of FIG. 5;

FIG. 9 is a schematic front view of a surgical fastener coil body;

FIG. 10 is a schematic top view of the surgical fastener coil body of FIG. 9;

FIG. 11 is a schematic perspective view of the surgical fastener coil body of FIG. 9;

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

A surgical fastener is provided for various surgical fastening applications. For example, the surgical fastener may be used to attach an implantable prosthesis, such as a soft tissue repair fabric, to tissue and/or muscle. Other non-limiting applications for the fastener may involve joining portions of tissue and/or muscle together, joining portions of tissue and/or muscle to bone, and/or joining an implantable prosthesis to bone.

In some embodiments, the surgical fastener may include a coil body and a separately manufactured head that is attached to the coil body. This arrangement may improve the manufacturability of the fastener and reduce costs, particularly as compared to costs associated with injection molding a complex surgical fastener. This arrangement may be particularly suited for manufacturing the head and coil body from different materials. However, embodiments in which the head and coil body are manufactured together as a single monolithic part are also contemplated.

Figure 12:
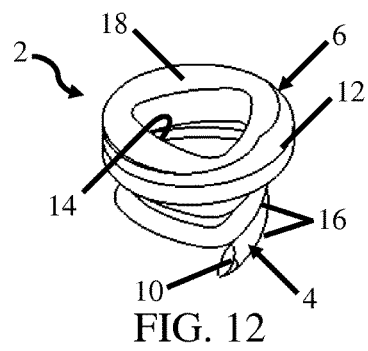
FIG. 12 is a schematic perspective view of a surgical fastener.
Figure 13:
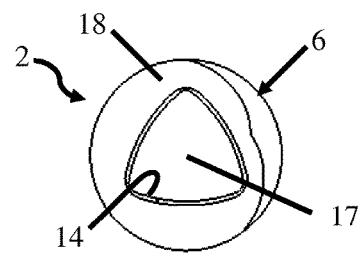
FIG. 13 is a schematic top view of the surgical fastener of FIG. 12.
Figure 14:
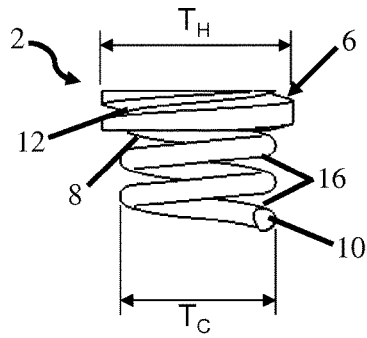
FIG. 14 is a schematic front view of the surgical fastener of FIG. 12.
Figure 15:
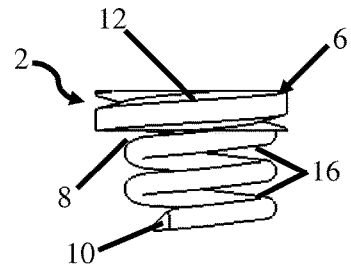
FIG. 15 is a schematic side view of the surgical fastener of FIG. 12.
Figure 16:
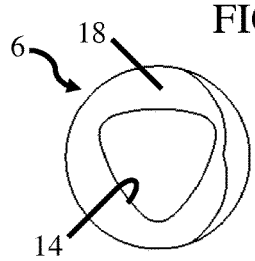
FIG. 16 is a schematic top view of a surgical fastener head.
Figure 17:
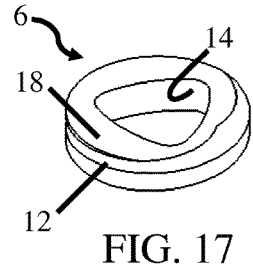
FIG. 17 is a schematic perspective view of the surgical fastener head of FIG. 16.
Figure 20:
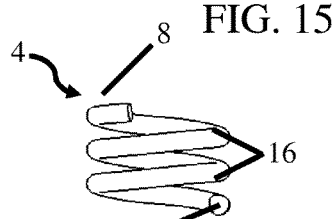
FIG. 20 is a schematic front view of a surgical fastener coil body.
Figure 18:
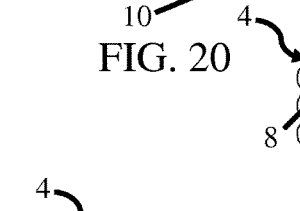
FIG. 18 is a schematic front view of the surgical fastener head of FIG. 16.
Figure 19:
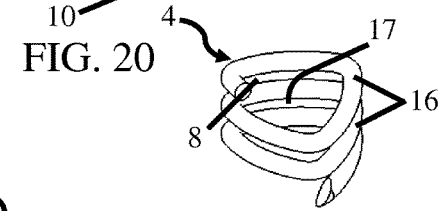
FIG. 19 is a schematic side view of the surgical fastener head of FIG. 16.
Figure 21:
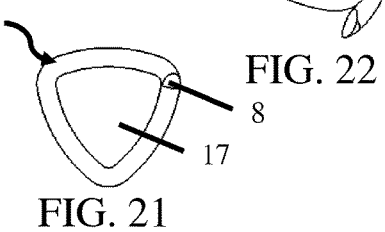
FIG. 21 is a schematic top view of the surgical fastener coil body of FIG. 20.
Figure 22:
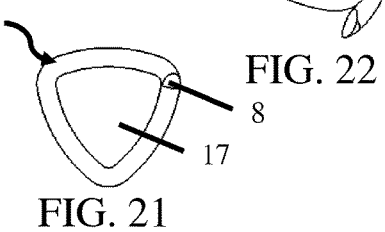
FIG. 22 is a schematic perspective view of the surgical fastener coil body of FIG. 20.

For the purposes of this application, a transverse dimension of the coil body or head generally refers to a dimension of the coil body or head within a plane that is perpendicular to a long axis of the surgical fastener when it is assembled (e.g. a diameter of a cylindrical coil body, a width of a rectangular head, the length of a side of a triangular coil body, etc. . . . ). For example, an outer transverse dimension of the coil body would refer to the lateral distance between opposing outer surfaces of the coil body and an inner transverse dimension of the coil body would refer to the lateral distance between opposing interior surfaces of the coil body. The outer transverse dimensions of the head $T_H$ and coil body $T_C$ in one embodiment are illustrated in FIGS. 3 and 14. The outer transverse dimensions correspond to the width of the head and the diameter of the coil body in FIG. 3 and the widths of the head and coil body in FIG. 14. It should be noted that in embodiments in which the head and/or the coil body are noncircular, the head and/or coil body may have both minimum and maximum transverse dimensions.

In a related embodiment, a transverse dimension of the head may be configured to be larger, such as wider or greater in diameter, than a transverse dimension of the coil body to engage and secure underlying material and/or tissue. The head may include at least one external thread adapted to engage with a corresponding internal thread of a delivery device.

Depending on the embodiment, the head may include a through hole adapted to receive a rod therethrough for guiding and/or driving the surgical fastener from the delivery device and into the implantable prosthesis and/or tissue. The through hole may have a non-circular configuration that corresponds to the shape of a non-circular rod. Alternatively, or in combination with a non-circular through hole, the coil body may define a channel have a non-circular configuration adapted to receive a correspondingly shaped non-circular rod. Thus, the non-circular through hole and/or coil body may have the same transverse dimensions such that they are engaged and rotated by the non-circular rod to rotate the surgical fastener for delivery and insertion of the fastener into the prosthesis and/or tissue. However, in some embodiments, the coil body may have a minimum inner transverse dimension that is larger than a maximum transverse dimension of the through hole of the head such that the coil body is not engaged by the non-circular rod.

While in some embodiments, the through hole and/or the channel of the coil body may have shapes that substantially complement the shape of the non-circular rod, the disclosure is not so limited. For example, only a portion of the rod may complement a shape of the through hole and/or the channel of the coil body. Thus the through hole and/or the coil body might be shaped such that they only interact with two flats located on opposing sides of a non-circular rod. Other appropriate geometries are also contemplated.

In one illustrative embodiment shown in FIGS. 1-11, the surgical fastener 2 may include a coil body 4 and a separately manufactured head 6 that is attached to a proximal end of the coil body 8. The distal end of the coil body 10 may be configured for penetrating an implantable prosthesis, tissue, muscle, and/or bone. In one embodiment, the distal end may include a sharp distal tip, although the distal end may employ any suitable configuration as should be appreciated by one of skill in the art.

Figure 23:
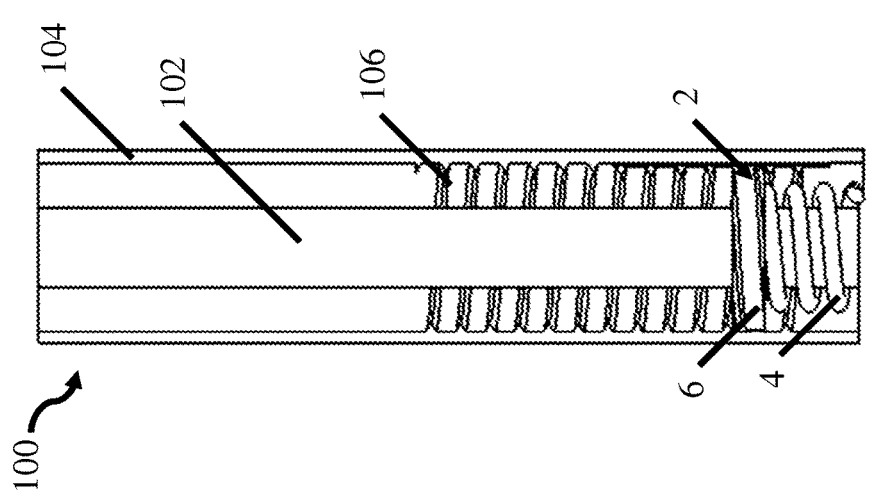
FIG. 23 is a schematic cross-sectional view of a delivery device and a surgical fastener prior to deployment.
Figure 24:
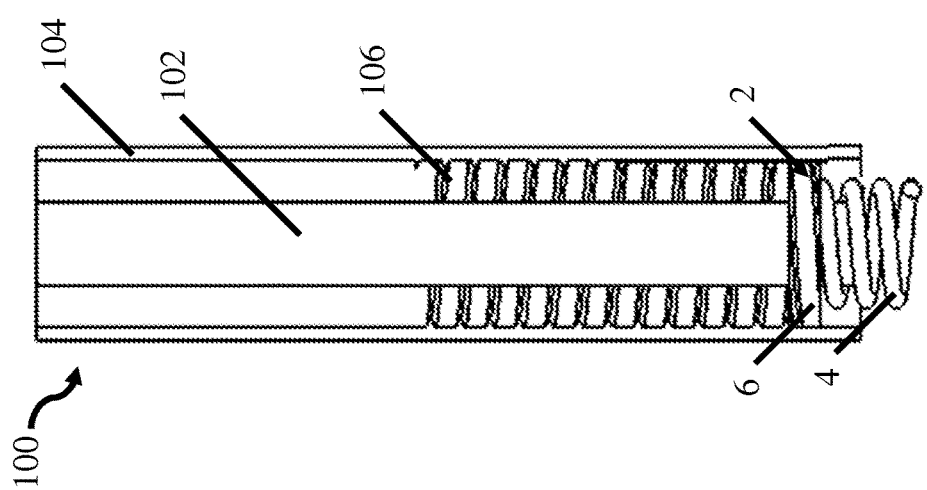
FIG. 24 is a schematic cross-sectional view of the delivery device and the surgical fastener of FIG. 23 during deployment.
Figure 25:
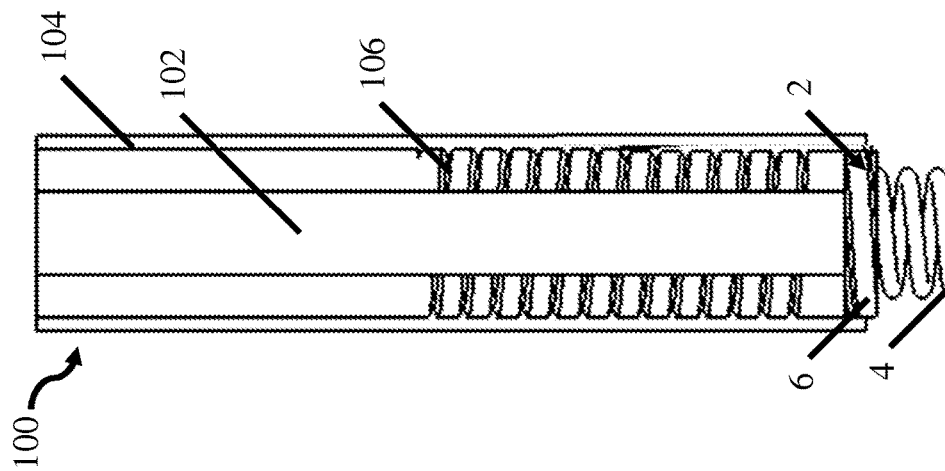
FIG. 25 is a schematic cross-sectional view of the delivery device and the surgical fastener of FIG. 23 after deployment.

As described in more detail below with respect to FIGS. 23-25, the head 6 and/or coil body 4 may be configured to cooperate with a drive element, such as a rod, of a delivery device that engages with and rotates the surgical fastener for delivering and inserting the fastener into an implantable prosthesis and/or tissue. In one embodiment, the head 6 includes at least one external thread 12 that corresponds to an internal thread of an outer tube or shaft of the delivery device within which may be housed one or more fasteners. Rotation of the head relative to the internal thread causes the fastener to be driven axially along the length of the rod, out of the shaft and into the prosthetic material and/or tissue.

In an illustrative embodiment also shown in FIGS. 1-8, the head 6 includes a non-circular through hole 14 for receiving a correspondingly shaped rod of the delivery device therethrough. As shown, the through hole 14 may have an elongated configuration with straight sides and curved ends that may be generally circular in shape. In this manner, the through hole 14 has a "double-D" shape. The through hole 14 is configured to closely conform to the shape of the delivery device rod, such as a double-D rod, so that rotation of the rod imparts rotation to the head for driving and inserting the fastener. However, embodiments in which the through hole only conforms to a portion of the shape of the delivery device rod are also possible.

As illustrated by FIGS. 9-11, the coil body 4 includes a plurality of coil windings 16 and a channel 17 defined by the coil body 4. As illustrated, the coil windings 16 may be arranged in a helical or spiral configuration suitable for driving the fastener into and through prosthetic material, tissue, muscle and/or bone. The coil body 4 may have a circular configuration, although other configurations are contemplated. The coil body may include any number of coil windings 16 with any desired spacing or pitch between the coil windings and any transverse dimension, including outer, inner and pitch diameters, suitable for a particular application as should be appreciated by one of skill. In one embodiment, the coil body 4 may include coil windings 16 having the same diameter. However, if desired, one or more of the coil windings 16 may have different transverse dimensions relative to each other. For example, the coil body 4 may employ coils 16 that decrease in size from the proximal end 8 toward the distal end 10 to form a coil body with a tapered shape.

The head may have any suitable configuration desired for a particular application. In one embodiment, the head includes a generally flat proximal face 18 and a generally flat opposite or distal face 20 from which extends the coil body 4. However, the distal and/or proximal faces 18 and 20 of the head 6 may have one or more generally flat, round, angled or beveled surfaces, or combinations thereof, as should be apparent to one of skill, as the current disclose is not limited to only the embodiments depicted in the figures.

In some embodiments, it may be desirable to employ a non-circular coil body defining a channel with a non-circular configuration that closely conforms to at least a portion of the shape and size of the delivery device rod and/or through hole so that rotation of the rod imparts rotation to the coil body for driving and inserting the fastener. The coil body including a non-circular channel may be utilized either in place of or in combination with a non-circular through hole. For example, a coil body including a non-circular channel and a head with a circular through hole might be used, or a coil body including a non-circular channel and a head with a non-circular through hole might be used.

In an illustrative embodiment shown in FIGS. 12-21, the fastener 2 includes a coil body 4 with a channel 17 with a polygonal configuration with at least three lobes, although the coil body and channel may employ any suitable non-circular configuration as should be apparent to one of skill in the art. As shown, the channel 4 may have a generally triangular shape. The distal end 10 of the coil body 4 includes a tip that may be located at a corner of the polygonal configuration. However, other corresponding locations of the tip are also contemplated. Similar to the previous embodiment, the head 6 attached to the coil body 4 may include an external thread 12.

In addition to the coil body, in some embodiments, the head 6 may also include a non-circular through hole 14 that corresponds to at least a portion of the shape and size of the channel 17 and coil body 4. In an illustrative embodiment, the through hole 14 has a polygonal configuration that matches the shape of the coil body 4 and the rod of the delivery device, not depicted. In this manner, rotation of the rod imparts rotation to the head 6 and the coil body 4 for driving and inserting the fastener 2. However, the through hole 14 may employ any suitable circular or non-circular configuration as should be apparent to one of skill. Additionally, the through hole and the channel may either be aligned or offset from one another as the current disclosure is not so limited.

In one embodiment the head may be attached to the coil body by molding the coil body and head together. For example, the head may be molded to a prefabricated coil body using an insert molding or over-molding process as should be apparent to one of skill. In one illustrative embodiment as shown in FIGS. 3, 4, 14, and 15, the coil body 4 may be attached to a portion of the head 6 located between the through hole 14 and the external thread 12 to allow the fastener 2 to receive the rod of the delivery device therethrough, not depicted. However, it is to be appreciated that the coil body may be attached to any suitable portion of the head using any appropriate attachment technique as should be apparent to one of skill.

In one embodiment, the surgical fastener may include a coil body having a length of approximately 3 mm (0.118 inches) to approximately 6.5 mm (0.256 inches) extending from the distal face of the head. The coil body may include approximately 2.5 turns to approximately 6 turns of coils having an outer transverse dimension of approximately 2.5 mm (0.098 inches) to approximately 4.9 mm (0.193 inches) for delivery through a 5 mm (0.197 inches) shaft with a pitch of approximately 0.7 mm to approximately 1.1 mm (0.03 inches to 0.045 inches). For a polygonal shaped coil body and corresponding channel, the lobes of the coil body are inscribed on a circle having such transverse dimensions. The head may include an external thread that corresponds to the internal thread of the delivery device. The head may have a thickness of approximately 0.51 mm (0.020 inches) to approximately 1.02 mm (0.04 inches). Of course, while specific dimensions are given above, the surgical fastener may employ a coil body and head having any suitable sizes and configurations for a desired application as should be apparent to one of skill in the art.

The surgical fastener may be made from one or more biocompatible materials that are suitable for a particular surgical application and is sterilized or sterilizable. The fastener components may be made from a non-absorbable material, an absorbable material or a combination of absorbable and non-absorbable materials. The components may be made from, and/or coated with, materials and/or include features that may resist tissue ingrowth and/or adhesions, permit tissue ingrowth and/or adhesions, or a combination thereof. The components may be made from metal, plastic and/or any other suitable materials as should be apparent to one of skill in the art.

In one embodiment, the head may be made from a plastic polymer including, but not limited to, polyether ether ketone (PEEK) or acetal, and the coil body may be made from a metal including, but not limited to, stainless steel, nitinol, or titanium. If desired, the head alone or the head and the coil body may be made from an absorbable metal and/or polymer.

In one exemplary embodiment, the surgical fastener may has an overall length of approximately 4.5 mm (0.177 inches) with a coil length extending from the head of approximately 3.5 mm (0.138 inches). The head has a thickness of approximately 1 mm (0.039 inches). The coil body is non-circular and has an inner transverse dimension at the lobes of approximately 3.8 mm (0.15 inches) and is made from 0.45 mm (0.018 inch) diameter metal wire to have a constant pitch of approximately 0.91 mm to 1.7 mm (0.036 inches to 0.042 inches). The external thread of the head may have the same pitch as the coil windings. However, embodiments in which the external thread of the head and the coil windings have different pitches are also contemplated.

The surgical fastener may be delivered to a surgical site using a delivery device that imparts rotation to the fastener and drives the fastener into prosthetic material, tissue, muscle, and/or bone. As shown in FIGS. 23-25, the delivery device 100 may include a rod 102 that extends along the length of an outer tube or shaft 104 for supporting and/or guiding one or more fasteners 2 within the shaft. The outer shaft 104 may include an internal thread 106 that corresponds to and engages the external thread of the head 6. The rod 102 may be configured with a non-circular shape that corresponds to and mates with the through hole of the head 6 and/or the coil body 4 to assist with delivery and installation of the fastener 2 with the delivery device 100. The delivery device 100 may use a rotatable rod 102 with a stationary shaft 104 that is configured to engage and rotate the head 6 and/or coil body 4 of each fastener 2, and thereby rotate each fastener 2 within the shaft 104. Rotation of the fastener 2 relative to the internal thread 106 of the shaft in turn provides a reactive thrust to the fastener causing the fastener to be driven in a distal direction along the length of the rod, out of the shaft and into the prosthetic material, bone, muscle, and/or tissue. However, it is to be appreciated that the surgical fastener 2 may be delivered using other arrangements and any suitable delivery device as should be apparent to one of skill in the art. For example, the currently disclosed surgical fasteners may be used with a laparoscopic device, an endoscopic device, a borescopic device, a catheter, a surgical instrument for use in "open" procedures, or any other appropriate surgical instrument.

While the embodiments described above, and depicted in the figures, have included a single external thread on the head, a plurality of external threads might be included on the head. Further, the individual threads may also include any number of turns, or partial turns. However, in some embodiments, it may be desirable to include a minimum amount of combined turns from the one or more threads such as one combined turn, two combined turns, or any other appropriate number of turns. For example, the head might include two external threads with at least a half turn each or three external threads with at least a third turn each.

It should also be understood that the foregoing description of various aspects of at least one embodiment of the invention are intended merely to be illustrative thereof and that other embodiments, modifications, and equivalents of the invention are within the scope of the invention recited in the claims appended hereto. Accordingly, the foregoing description and drawings are by way of example only.

What is claimed is:
1. A surgical fastener comprising:
  a coil body including a plurality of coil windings, the coil body having a proximal end and a distal end; and
  a separate head attached to the proximal end of the coil body and rotationally fixed relative to the coil body, the head including at least one external thread with one or more turns to engage with a corresponding internal thread of a delivery device, the head further including a through hole with a non-circular cross section adapted to receive a rod therethrough to guide and/or drive the surgical fastener from the delivery device, wherein the through hole extends from a first face of the head to a second opposing face of the head, wherein a proximal face of the head is substantially flat, and wherein the non-circular cross-section is constant along at least a portion of a length of the through hole.

2. The surgical fastener according to claim 1, wherein the head is manufactured separately from the coil body.

3. The surgical fastener according to claim 1, wherein the coil body has a circular helical configuration.

4. The surgical fastener according to claim 1, wherein the coil body defines a non-circular channel therethrough.

5. The surgical fastener according to claim 4, wherein the non-circular channel of the coil body has a polygonal configuration.

6. The surgical fastener according to claim 5, wherein the distal end of the coil body includes a tip that is located at a corner of the polygonal configuration of the non-circular channel of the coil body.

7. The surgical fastener according to claim 5, wherein the coil body has a tri-lobe configuration.

8. The surgical fastener according to claim 5, wherein the non-circular cross section of the through hole is the same shape as the polygonal configuration of the coil body.

9. The surgical fastener according to claim 1, wherein the coil body has a minimum inner transverse dimension that is larger than a maximum transverse dimension of the through hole of the head.

10. The surgical fastener according to claim 1, wherein the coil body is positioned coaxial with the through hole of the head.

11. The surgical fastener according to claim 1, wherein the head and the coil body are fabricated from different materials.

12. The surgical fastener according to claim 11, wherein the head comprises a plastic or metal.

13. The surgical fastener according to claim 12, wherein the coil body comprises a plastic or metal.

14. The surgical fastener according to claim 1, wherein the through hole has a polygonal shape.

15. The surgical fastener according to claim 1, wherein a pitch of the plurality of coil windings on the coil body is constant.

16. The surgical fastener of claim 1, wherein the at least one external thread of the head and the plurality of coil windings have different pitches.

17. The surgical fastener of claim 1, wherein the non-circular cross-section is constant along an entire length of the through hole.

18. The surgical fastener of claim 1, wherein the head does not extend into an interior channel of the coil body.

19. A surgical fastener comprising:
a coil body including a plurality of coil windings, the coil body having a proximal end and a distal end; and
a separate head attached to the proximal end of the coil body and rotationally fixed relative to the coil body, the head including at least one external thread to engage with a corresponding internal thread of a delivery device, the head further including an unobstructed through hole with a non-circular cross section adapted to receive a rod therethrough to guide and/or drive the surgical fastener from the delivery device, wherein the head has a maximum outer transverse dimension that is larger than a maximum outer transverse dimension of the coil body when the coil body is in a relaxed state;
wherein the through hole extends from a first face of the head to a second opposing face of the head; and
wherein the through hole includes straight sides and curved ends, wherein the curved ends include a curved arc extending from a first side of the through hole to a second opposing side of the through hole.

20. The surgical fastener according to claim 19, wherein the head is manufactured separately from the coil body.

21. The surgical fastener according to claim 19, wherein the coil body has a circular helical configuration.

22. The surgical fastener according to claim 19, wherein the coil body has a minimum inner transverse dimension that is larger than a maximum transverse dimension of the through hole of the head.

23. The surgical fastener according to claim 19, wherein the coil body is positioned coaxial with the through hole of the head.

24. The surgical fastener according to claim 19, wherein the head and the coil body are fabricated from different materials.

25. The surgical fastener according to claim 24, wherein the head comprises a plastic or metal.

26. The surgical fastener according to claim 25, wherein the coil body comprises a plastic or metal.

27. The surgical fastener according to claim 19, wherein the non-circular cross section of the through hole corresponds to a shape of the rod.

28. The surgical fastener according to claim 19, wherein a pitch of the plurality of coil windings on the coil body is constant.

29. The surgical fastener of claim 19, wherein the through hole has an elongated shape with straight sides and curved ends.

30. The surgical fastener of claim 19, wherein the at least one external thread of the head and the plurality of coil windings have different pitches.

31. The surgical fastener of claim 19, wherein the non-circular cross-section is constant along a length of the through hole.

32. The surgical fastener of claim 19, wherein the head does not extend into an interior channel of the coil body.

* * * * *